United States Patent
Ahn

(10) Patent No.: US 6,645,778 B2
(45) Date of Patent: Nov. 11, 2003

(54) METHOD FOR THE PREPARATION OF FERROELECTRIC SEMICONDUCTIVE COATING AND APPARATUS FOR REMOVING ENVIRONMENTAL AIR POLLUTANTS USING THIS COATING AND ELECTRIC POWER

(76) Inventor: Gil Hong Ahn, 419-25 Oncheon 2 Dong, Dongrae Gu, Busan (KR)

( * ) Notice: Subject to any disclaimer, the term of this patent is extended or adjusted under 35 U.S.C. 154(b) by 0 days.

(21) Appl. No.: 09/798,540

(22) Filed: Mar. 2, 2001

(65) Prior Publication Data

US 2002/0039798 A1 Apr. 4, 2002

(51) Int. Cl.[7] ............................................... H01L 21/00
(52) U.S. Cl. .................. 438/3; 438/905; 427/376.2; 422/4
(58) Field of Search ............................ 438/3, 905, 909; 422/4; 95/59; 427/376.2, 126.3

(56) References Cited

U.S. PATENT DOCUMENTS

| | | | | |
|---|---|---|---|---|
| 4,001,102 A | * | 1/1977 | Batha et al. | |
| 5,820,658 A | * | 10/1998 | Kim et al. | 95/228 |
| 5,865,879 A | * | 2/1999 | Lee | 95/273 |
| 6,315,501 B1 | * | 11/2001 | Yagai et al. | 406/198 |

* cited by examiner

Primary Examiner—Caridad Everhart
(74) Attorney, Agent, or Firm—Knobbe, Martens, Olson & Bear, LLP

(57) ABSTRACT

Disclosed is a method for preparing ferroelectric semiconductive coatings which is capable of coating the ferroelectric semiconductor onto a metal and forming electron-hole pairs on the surface of the ferroelectric semiconductor by using 440 V and 30K~100K Hz alternating current electric energy of a high voltage and a high frequency as an energy source, based upon an energy level difference between the semiconductor and the metal, whereby it can exhibit an effective surface reaction in the range of the oxidation and reduction reaction even in the closed space where no ultraviolet irradiation occurs.

8 Claims, 4 Drawing Sheets

METHOD FOR THE PREPARATION OF FERROELECTRIC SEMICONDUCTIVE COATING AND APPARATUS FOR REMOVING ENVIRONMENTAL AIR POLLUTANTS USING THIS COATING AND ELECTRIC POWER

BACKGROUND OF THE INVENTION

1. Field of the Invention

The present invention relates to a method for preparing a ferroelectric semiconductive coating and to an apparatus for removing environmental air pollutants using this coating and electric power. More particularly, the present invention relates to an air cleaning apparatus which utilizes a ferroelectric semiconductor coated with a metal. The air cleaning reaction device can be used for air cleaning within a room or in industrial areas where noxious gases are generated. The apparatus and the method have various advantages such as cost reduction by using electric power as an energy source, increased efficiency, light weight, simplicity, a rapid treatment for large volumes of air, and improved safety.

2. Description of the Related Art

As well known, a large number of air cleaners are available, most of which utilize a filter. However, although these air cleaners can remove foreign materials such as dust, they fail to completely remove air pollutants which are fine particles or gases, for example, noxious gases, gases containing heavy metals, etc. Therefore, advanced types of air cleaners employ a plasma generator or an electron beam generator to burn the air pollutants. However, even these advanced types of air cleaners do not completely clean the polluted air.

Another air cleaner utilizes titanium oxide as a semiconductive material catalyst. Heat is applied to the catalyst to cause adsorption and dissolution of noxious organic compounds and non-combustion hydrocarbon compounds on the catalyst. However, applying heat to cause catalytic combustion leads to the following problems: the area occupied by the apparatus is extremely large; and the energy cost is high.

If semiconductive materials absorb energy exceeding the energy band gap, conduction electrons in the semiconductive material are excited and move from a valence band to a conduction band. Positive holes are left in the valence band, and electrons are excited into the conduction band, thereby forming electron-hole pairs. At this time, the behavior of the electron-hole pairs of the semiconductor, to which an electric field is applied, prolongs the moving life of a carrier to delay re-coupling, and the produced electron-hole pairs join in a reaction with the compounds.

In such semiconductive materials, the titanium oxide having a negative ion lack type of nonstoichiometric shear structure is an effective material that can be employed as a catalyst, and if it absorbs the band gap energy of 3.2 electron volts or more and/or light having 250–400 nanometer wavelengths, the conduction electrons are excited, thereby forming the electron-hole pairs. The excited titanium oxide itself does not dissolve. The positive holes produce an OH radical as a strong oxidizing agent, thereby decomposing polluted materials through an oxidation reaction. The electrons are utilized for the reduction reaction.

Therefore, the titanium oxide as the photo-catalyst adsorbs noxious organic materials, non-combustion hydrocarbon compounds, etc. contained in the air or water to decompose the adsorbed contents into the following state equation: catalyst/band gap energy:

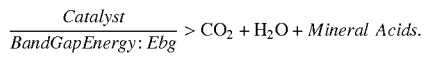

$$\frac{Catalyst}{BandGapEnergy:Ebg} > CO_2 + H_2O + Mineral\ Acids.$$

Also, the titanium oxide catalyst has characteristics suitable for reactions such as, sterilization and antibiosis, burning removal and deodorization of odor, hot wave reflection, cigarette nicotine decomposition and removal, self-cleaning, and oil decomposition and therefore, has already been put into practical use in various industrial fields.

In order to induce an appropriate reaction, a conventional air cleaning apparatus is generally subjected to ultraviolet irradiation to supply the band gap energy. However, upon ultraviolet irradiation the catalytic reaction is exhibited only on the section of the semiconductor where light is absorbed. Efficiency is low due to the straightness, reflection, and refraction of the light.

Therefore, the conventional air cleaning apparatus has numerous limitations when applied to various industrial spots. For example, due to various kinds of restrictions such as the problem of installing a light source, the thickness of the optical catalyst coating, environmental factors in placing the installation, installation cost, structural problems and so on, the conventional air cleaning apparatus is not widely applied in industrial areas, even though it is effective in catalyzing the decomposition reactions.

SUMMARY OF THE INVENTION

It is, therefore, an object of the present invention to provide a method for preparing a ferroelectric semiconductive coating which is capable of bonding with a metal and which is capable of forming electron-hole pairs on the surface of the ferroelectric semiconductor with 440 V and 30K–100K Hz alternating current (AC) electric energy having high voltage and high frequency as an energy source, based upon the energy level difference between the semiconductor and the metal, whereby it can exhibit an effective surface reaction in the range of the oxidation and reduction reactions even in an enclosed space where no ultraviolet irradiation occurs.

It is another object of the present invention to provide a ferroelectric semiconductive coating capable of achieving a light weight and simplicity of the structure and carrying out rapid treatment for a large volume of air.

It is still another object of the present invention to provide a method for preparing a ferroelectric semiconductive coating on a metal material, applying electric power generated by the application of an alternating current (AC) voltage to the metal material and the ferroelectric semiconductive coating, and to provide an apparatus for removing environmental air pollutants using the coating and electric power.

DETAILED DESCRIPTION OF THE PREFERRED EMBODIMENT

Figure 1:
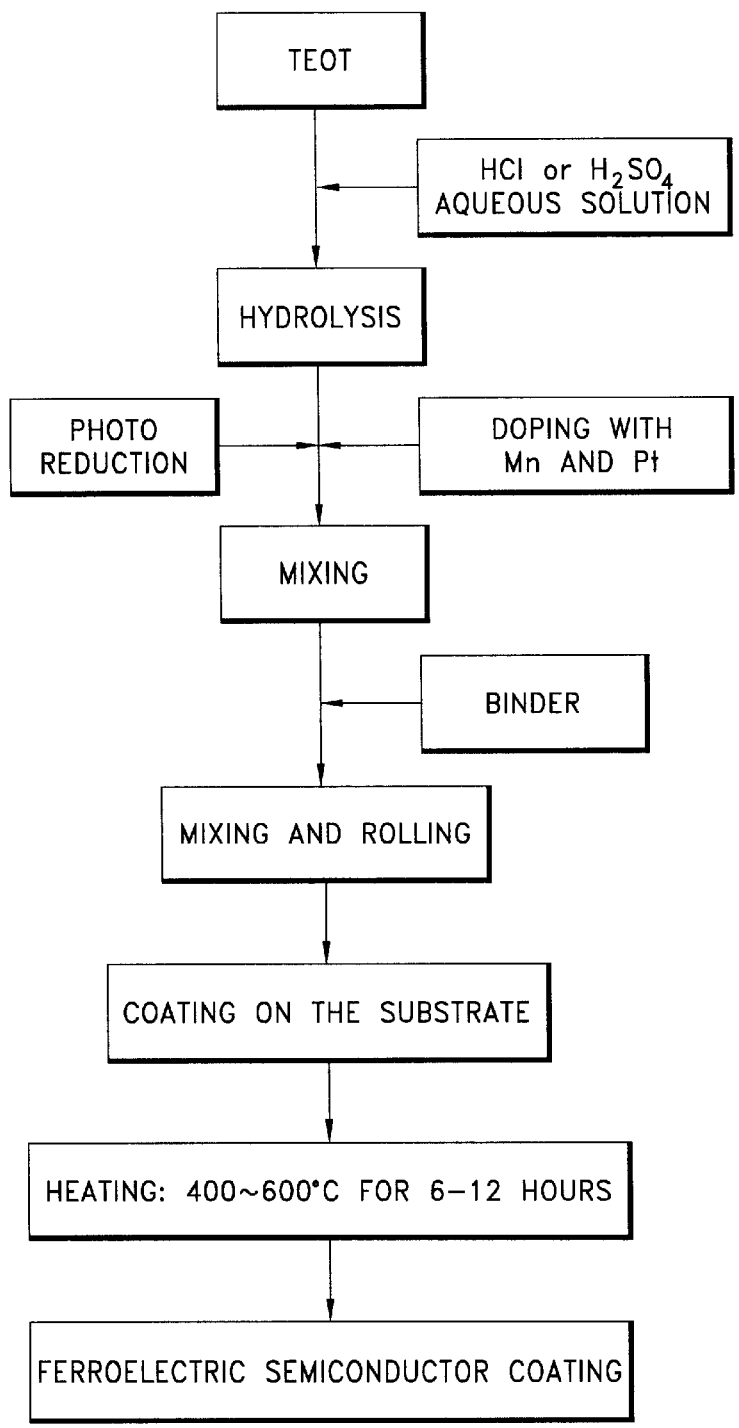
FIG. 1 is a flowchart illustrating the processes for preparing a ferroelectric semiconductive coating according to a first embodiment of the present invention.

Referring to FIG. 1, the processes for preparing a ferroelectric semiconductive coating according to a first embodiment of the present invention are described.

First process: TEOT (Tetraethyl orthotitanate) is mixed with water/alkoxide in a mol ratio of about 10 to about 50. The mixture is stirred for about 2–8 hours to decompose the mixture in water. A water solution of about 1–7 wt. % hydrochloric acid or sulfuric acid is poured into the mixture.

Second process: On the basis of titanium oxide as 100 mole %, the titanic acid oxide produced at the first process is mixed into a methanol solution, and an oxygen producing activating agent containing about 0.1–0.7 mol % manganese in 12.5 wt. % manganese chloride water solution, about 1.5–3.5 mol % bismuth in 7 wt. % bismuth chloride water solution, about 0.5–1.5 mol % nickel in 11.7 wt. % nickel chloride water solution, and about 5–8 wt. % strontium is mixed with the titanic acid oxide.

Third process: In the mixture produced in the second process, a hydrocarbon adsorption activating agent containing about 0.1–0.5 mol % of 0.5 wt. % platinum chloride water solution, about 2–10 mol % of 0.5 wt. % silver chloride dissolved in 10% aqueous ammonia, about 0.5–5.0 mol % of 5 wt. % tungsten trioxide dissolved in 7.5 wt. % lithium hydroxide solution and about 1–15 mol % of 5 wt. % molybdenum oxide are mixed with each other. At this time, intercalation of the lithium ion increases the electric conductivity of the coating, and the conduction band moves to a positive value.

Fourth process: The energy band gap of the titanium oxide is adjusted by mixing about 1–5 mol % of an oxidation type of cobalt oxide having an oxygen carrier function into the mixture produced in the third process.

Fifth process: The coating composition from the fourth process is coated on a metal to have a dry film thickness of about 15–30 micrometers and is heated for about 6–12 hours at a temperature of about 400–600° C., thereby producing the ferroelectric semiconductive coating.

According to the method for preparing the ferroelectric semiconductive coatings, as described above, the coating is applied on the surface of the metal, such that a negative contact or Schottky barrier bonding is achieved in accordance with an operation function between the metal and the coating. If a voltage is applied to the metal to which the coating has been applied on the surface thereof, Zener breakdown or electron-inclination breakdown occurs by a current-voltage characteristic and thus, the conduction electrons are excited. At this time, the electron-hole pairs produced by the generation of the excitation by the ionosphere collision on the ferroelectric semiconductive particles join in the oxidation and reduction reactions.

In other words, from the micro viewpoint, the electron-hole pairs are produced on the individual particles of the ferroelectric semiconductor, but from the macro viewpoint, the coatings take one electron-hole pair by the injection of minor carriers, thereby drastically increasing the efficiency of the surface chemical reaction.

Figure 2:
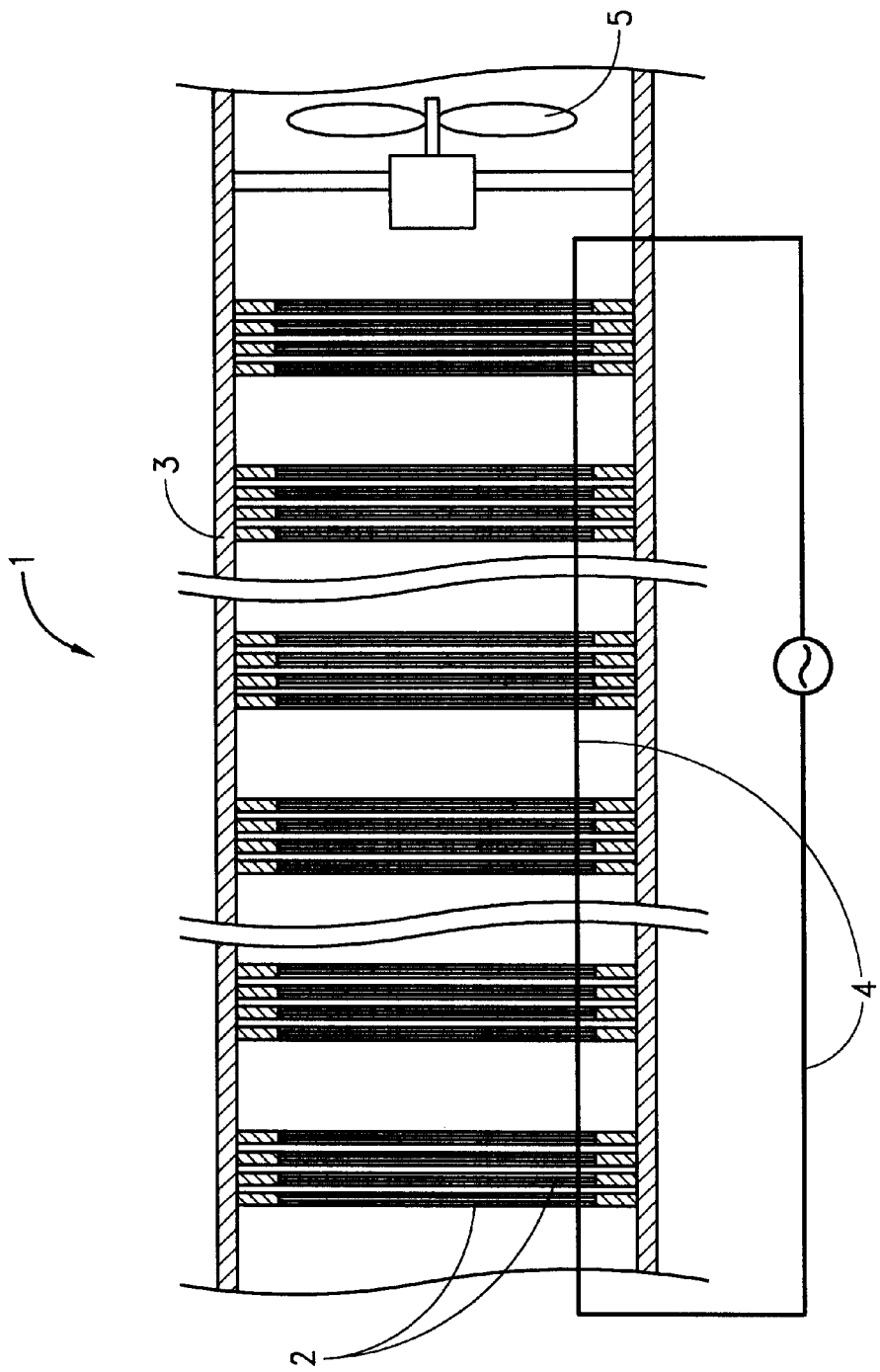
FIG. 2 is a side sectional view illustrating an air cleaning reaction device for removing environmental air pollutants, such as, for example, volatile organic materials, non-combustion hydrocarbon compounds and all kinds of bad odors, according to a second embodiment of the present invention.
Figure 3:
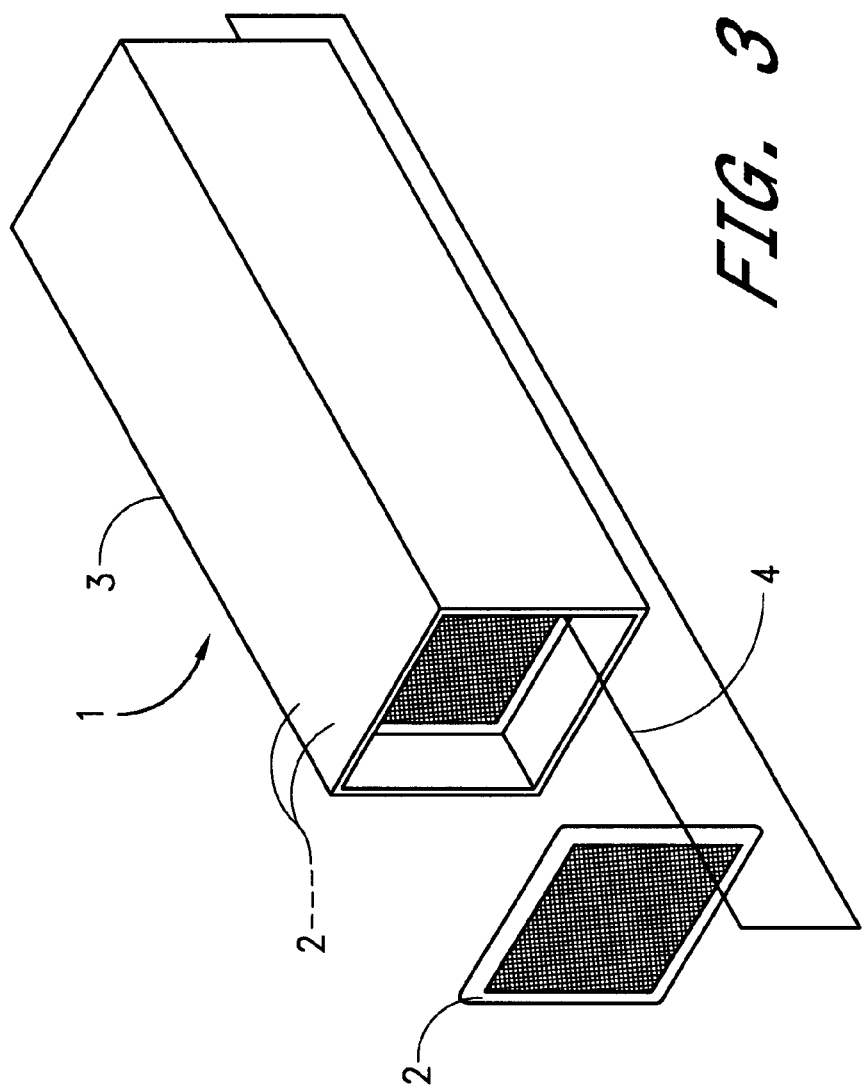
FIG. 3 is a partly exploded and perspective view of the air cleaning reaction device of FIG. 2.

FIG. 2 is a side sectional view illustrating an air cleaning reaction device 1 according to a second embodiment of the present invention, using the ferroelectric semiconductor on which a coating has been formed.

The ferroelectric semiconductor plates 2 on which the coating is formed are arranged at intervals of about 0.6–0.8 inch to thereby form a plurality of groups and next, the arranged groups are equally spaced apart within a duct 3 through which a discharge gas is passed. The arranged ferroelectric semiconductor plate groups are connected to a power line 4 applying 440 V and about 30K–100K Hz alternating current electric energy of a high voltage and a high frequency, based upon the energy level difference between the semiconductor and the metal. Further, a blowing fan 5 is provided on the one side of the device 1 for blowing the air into the interior of the ferroelectric semiconductor plates 2 in a forced manner.

In the embodiment shown in FIG. 2, each of the ferroelectric semiconductor plates 2 has a window shape having diamond-shaped or lattice-shaped bars in the square outer frame and has a net structure through which air is passed, where the coating is formed on the net.

Under the above construction, if the air containing noxious gases are passed through the air cleaning reaction device 1, the electrons and the positive holes of the semiconductor receive the force $$F_1 = \pm Q_1 E_1 = \pm \frac{Q_1 q_1}{4\pi\gamma 2\varepsilon}$$

(wherein ε represents a dielectric constant) by a displacement current electric field $E_1$ produced by the voltage caused by a rectification action of semiconductor physical characteristics.

The displacement current produced at the time when the voltage is applied to the semiconductor generates an electromagnetic field. The electromagnetic force generated by the electromagnetic field produces an electromotive force in a membrane to thereby accelerate the formation of the electron-hole pairs and generate a force $F_2=\pm Q_2 E_2=\pm Q_2 E_0$ Cos wt. The above forces $F_1$ and $F_2$ are synthesized based upon the principle of electric superposition and cause the electromotive force by the force F total=$(\pm F_1)+(\pm F_2)$ in a vector direction. That is, the ferroelectric semiconductive coatings join in the oxidation and reduction reaction by the electromotive force $$E = (\pm F_1) + \left(\pm \frac{d\phi}{dt}\right).$$

Therefore, the surface of the ferroelectric semiconductor is subjected to the following chemical surface reactions:

(a)

$H_2O + h^+ \rightarrow 2 H^+ + \frac{1}{2} O_2$ $H_2O + h^+ \rightarrow H^+ + .OH$ (OH Radical)

Figure 4:
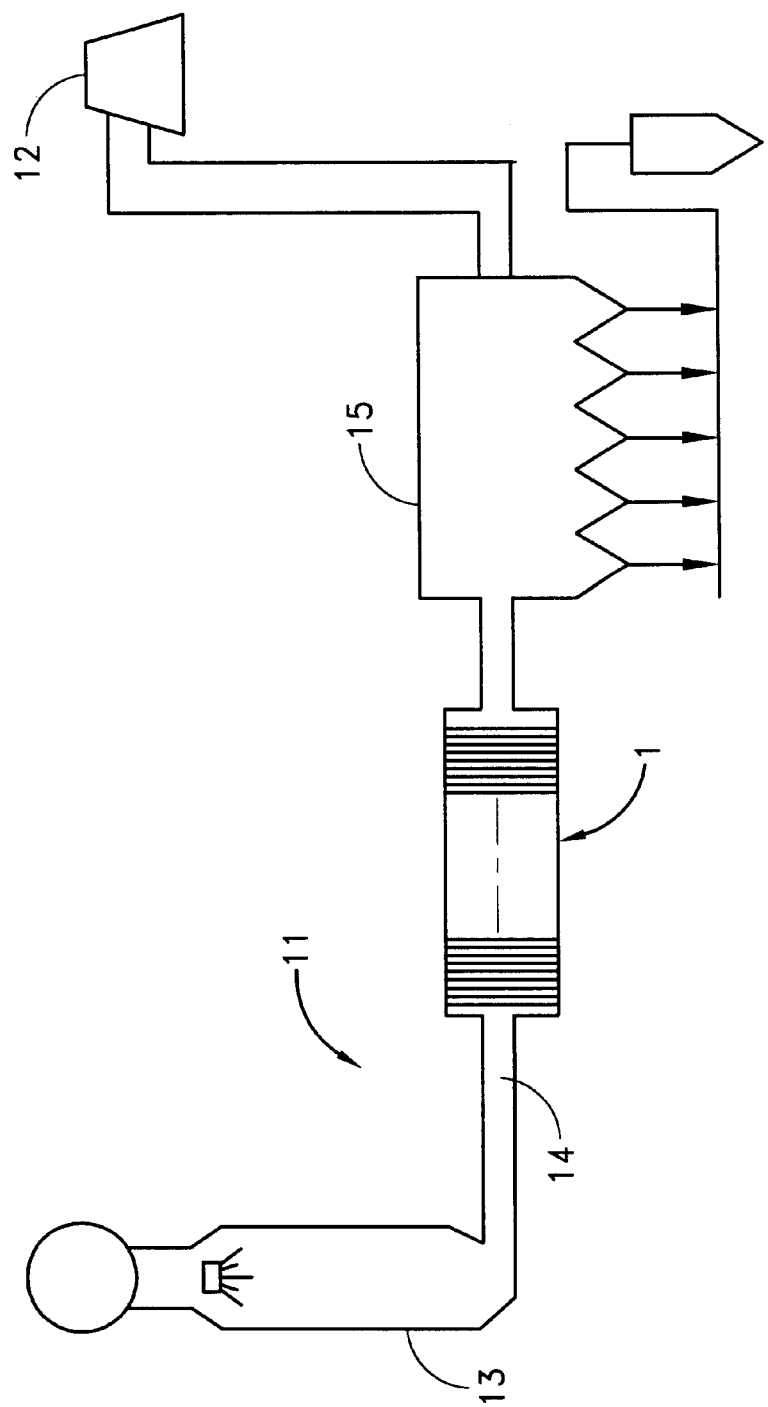
FIG. 4 is a schematic view illustrating an air cleaning apparatus including the air cleaning reaction device of FIG. 2, according to a third embodiment of the present invention, where the air cleaning apparatus is used for removing polluted discharge gas containing nitrogen oxide, organic chlorine compounds (dioxin, environmental hormone, etc.), or non-combustion hydrocarbon compounds.

$.OH + h^+ \rightarrow OH$ $2 OH \rightarrow (O) + H_2O$ (b) $h^+ \rightarrow h^+$ trap ($h^+$ trap: the hole is carried out on the surface, which directly joins in the oxidation reaction). The formed radicals react to the compounds and exhibit the following reactions, thereby being removed:

(a) $NO_x + .OH \rightarrow H^+ + NO_3^- \rightarrow H^+ NO_3^-$ (b) $Cl^- + .OH \rightarrow HOCl \rightarrow H^+ Cl^-$ (c) $H-C + .OH \rightarrow CO_2 + H_2O$ FIG. 4 is a schematic view illustrating an air cleaning apparatus 11 on which the air cleaning reaction device 1 manufactured in accordance with the second embodiment is mounted, according to a third embodiment of the present invention.

In construction, the air cleaning reaction device 1 is mounted in a path 14 connecting a smokestack 12 and a water spray cooling tower 13. A residuum collector 15 is provided on one side of the air cleaning reaction device 1.

If the above apparatus is applied to the industrial spots where the noxious gases are generated, it can remove fine noxious components. In operation, calcined lime and water is sprayed into the spray cooling tower 13 to partly absorb $SO_x$ and $NO_x$ and next, the air cleaning reaction device 1 converts the remaining $NO_x$ and chlorine compounds into acids such as nitric acid, hydrochloric acid, etc.

As set forth in the foregoing, an air cleaning reaction device according to the present invention can be manufactured with compact equipment with the help of the supply of an electric energy source and also excite conduction electrons to cause a surface chemical reaction. In addition, the air cleaning reaction device can rapidly treat the amount of air of a large capacity and a high density with the help of a fast reaction speed and if membranes are superposed in multi-step manner, the air cleaning reaction device can be configured to reduce the amount of energy consumed, thereby optimizing the reaction efficiency. Moreover, it exhibits a high efficiency in removing the bad odor out of the discharged gas. Further, it removes the organic compounds and treats the removed materials in a simple manner.

Various modifications and alterations of this invention will be apparent to those skilled in the art without departing from the scope and spirit of this invention. It should be understood that the invention is not limited to the embodiments disclosed herein, and that the claims should be interpreted as broadly as the prior art allows.

What is claimed is:

1. A method for preparing a ferroelectric semiconductive coating, comprising the steps of:
   (a) mixing tetraethyl orthotitanate with a water/alkoxide mixture in a molar ratio of between 10–50 to form a mixture, stirring the mixture for about 2–8 hours to decompose the mixture, and adding a water solution of 1 to 7 wt. % hydrochloric acid or sulfuric acid to the decomposed mixture to form titanic acid oxide;
   (b) mixing the titanic acid oxide produced in step (a) with a methanol solution, adding an oxygen producing activating agent containing about 0.1–0.7 mole % manganese in 12.5 wt. % manganese chloride water solution, about 1.5–3.5 mole % bismuth in 7 wt. % bismuth chloride water solution, about 0.5–1.5 mole % nickel in 11.7 wt. % nickel chloride water solution and about 5–8 wt. % strontium, where the mole %'s in the oxygen producing activating agent are on the basis of titanium oxide as 100 mole %;
   (c) adding to the product of step (b) a hydrocarbon adsorption activating agent containing about 0.1–0.5 mole % of 0.5 wt. % platinum chloride water solution, about 2–10 mole % of 0.5 wt. % silver chloride dissolved in 10% aqueous ammonia, about 0.5–15.0 mole % of 5 wt. % tungsten trioxide dissolved in 7.5 wt. % aqueous lithium hydroxide and about 1–15 mole % of 5 wt. % molybdenum oxide and mixing the product of step (b) with the hydrocarbon adsorption activating agent to form a coating material, wherein intercalation of the lithium ion substantially improves the electric conductivity of the coating material and moves a conduction band of said coating material to a positive value;
   (d) adding about 1–5 mole % of an oxidation type of cobalt oxide having an oxygen carrier function to the product of step (c), thereby adjusting the energy band gap of the titanium oxide;
   (e) dispersing sufficient product from step (d) on a metal to produce a coating on said metal having a thickness of about 15–30 micrometers after drying; and
   (f) heating the coating for about 6–12 hours at a temperature of about 400–600° C., thereby producing the ferroelectric semiconductive coating.

2. An air cleaning reaction device comprising:
   a plurality of ferroelectric semiconductor plates within a duct through which a discharge gas is passed;
   a power line for connecting the arranged ferroelectric semiconductor plate groups to 440 V and about 30K–100K Hz alternating current electric energy of a high voltage and a high frequency; and
   a blowing fan provided on the one side of said device, for blowing the gas over said ferroelectric semiconductor plates in said duct in a forced manner,
   wherein the plurality of ferroelectric conductor plates comprise a ferroelectric semiconductive coating prepared by:
      (a) mixing tetraethyl orthotitanate with a water/alkoxide mixture in a molar ratio of between 10–50 to form a mixture, stirring the mixture for about 2–8 hours to decompose the mixture, and adding a water solution of 1 to 7 wt. % hydrochloric acid or sulfuric acid to the decomposed mixture to form titanic acid oxide;
      (b) mixing the titanic acid oxide produced in step (a) with a methanol solution, adding an oxygen producing activating agent containing about 0.1–0.7 mole % manganese in 12.5 wt. % manganese chloride water solution, about 1.5–3.5 mole % bismuth in 7 wt. % bismuth chloride water solution, about 0.5–1.5 mole % nickel in 11.7 wt. % nickel chloride water solution and about 5–8 wt. % strontium, where the mole %'s in the oxygen producing activating agent are on the basis of titanium oxide as 100 mole %;
      (c) adding to the product of step (b) a hydrocarbon adsorption activating agent containing about 0.1–0.5 mole % of 0.5 wt. % platinum chloride water solution, about 2–10 mole % of 0.5 wt. % silver chloride dissolved in 10% aqueous ammonia, about 0.5–15.0 mole % of 5 wt. % tungsten trioxide dissolved in 7.5 wt. % aqueous lithium hydroxide and about 1–15 mole % of 5 wt. % molybdenum oxide and mixing the product of step (b) with the hydrocarbon adsorption activating agent to form a coating material, wherein intercalation of the lithium ion substantially improves the electric conductivity of the coating material and moves a conduction band of said coating material to a positive value;
      (d) adding about 1–5 mole % of an oxidation type of cobalt oxide having an oxygen carrier function to the product of step (c), thereby adjusting the energy band gap of the titanium oxide;
      (e) dispersing sufficient product from step (d) on a metal to produce a coating on said metal having a thickness of about 15–30 micrometers after drying; and
      (f) heating the coating for about 6–12 hours at a temperature of about 400–600° C., thereby producing the ferroelectric semiconductive coating.

3. The air cleaning reaction device of claim 2, wherein said plurality of ferroelectric semiconductor plates are arranged at intervals of about 0.6–0.8 inch.

4. The air cleaning reaction device of claim 3, wherein said plurality of ferroelectric semiconductor plates form a plurality of groups.

5. The air cleaning reaction device of claim 4, wherein said plurality of groups are equally spaced.

6. An air cleaning apparatus using a ferroelectric semiconductor on which a coating is formed, said apparatus comprising:
- an air cleaning reaction device mounted on a path communicating a smokestack and a spray cooling tower; and
- a residuum collector provided on the one side of said air cleaning reaction device, wherein said coating is formed by a method comprising:
  - (a) mixing tetraethyl orthotitanate with a water/alkoxide mixture in a molar ratio of between 10–50 to form a mixture, stirring the mixture for about 2–8 hours to decompose the mixture, and adding a water solution of 1 to 7 wt. % hydrochloric acid or sulfuric acid to the decomposed mixture to form titanic acid oxide;
  - (b) mixing the titanic acid oxide produced in step (a) with a methanol solution, adding an oxygen producing activating agent containing about 0.1–0.7 mole % manganese in 12.5 wt. % manganese chloride water solution, about 1.5–3.5 mole % bismuth in 7 wt. % bismuth chloride water solution, about 0.5–1.5 mole % nickel in 11.7 wt. % nickel chloride water solution and about 5–8 wt. % strontium, where the mole %'s in the oxygen producing activating agent are on the basis of titanium oxide as 100 mole %;
  - (c) adding to the product of step (b) a hydrocarbon adsorption activating agent containing about 0.1–0.5 mole % of 0.5 wt. % platinum chloride water solution, about 2–10 mole % of 0.5 wt. % silver chloride dissolved in 10% aqueous ammonia, about 0.5–15.0 mole % of 5 wt. % tungsten trioxide dissolved in 7.5 wt. % aqueous lithium hydroxide and about 1–15 mole % of 5 wt. % molybdenum oxide and mixing the product of step (b) with the hydrocarbon adsorption activating agent to form a coating material, wherein intercalation of the lithium ion substantially improves the electric conductivity of the coating material and moves a conduction band of said coating material to a positive value;
  - (d) adding about 1–5 mole % of an oxidation type of cobalt oxide having an oxygen carrier function to the product of step (c), thereby adjusting the energy band gap of the titanium oxide;
  - (e) dispersing sufficient product from step (d) on a metal to produce a coating on said metal having a thickness of about 15–30 micrometers after drying; and
  - (f) heating the coating for about 6–12 hours at a temperature of about 400–600° C., thereby producing the ferroelectric semiconductive coating.

7. A method for removing environmental air pollutants from a gas stream comprising:
- providing a plurality of ferroelectric semiconductor plates comprising a coating formed by a method comprising:
  - (a) mixing tetraethyl orthotitanate with a water/alkoxide mixture in a molar ratio of between 10–50 to form a mixture, stirring the mixture for about 2–8 hours to decompose the mixture, and adding a water solution of 1 to 7 wt. % hydrochloric acid or sulfuric acid to the decomposed mixture to form titanic acid oxide;
  - (b) mixing the titanic acid oxide produced in step (a) with a methanol solution, adding an oxygen producing activating agent containing about 0.1–0.7 mole % manganese in 12.5 wt. % manganese chloride water solution, about 1.5–3.5 mole % bismuth in 7 wt. % bismuth chloride water solution, about 0.5–1.5 mole % nickel in 11.7 wt. % nickel chloride water solution and about 5–8 wt. % strontium, where the mole %'s in the oxygen producing activating agent are on the basis of titanium oxide as 100 mole %;
  - (c) adding to the product of step (b) a hydrocarbon adsorption activating agent containing about 0.1–0.5 mole % of 0.5 wt. % platinum chloride water solution, about 2–10 mole % of 0.5 wt. % silver chloride dissolved in 10% aqueous ammonia, about 0.5–15.0 mole % of 5 wt. % tungsten trioxide dissolved in 7.5 wt. % aqueous lithium hydroxide and about 1–15 mole % of 5 wt. % molybdenum oxide and mixing the product of step (b) with the hydrocarbon adsorption activating agent to form a coating material, wherein intercalation of the lithium ion substantially improves the electric conductivity of the coating material and moves a conduction band of said coating material to a positive value;
  - (d) adding about 1–5 mole % of an oxidation type of cobalt oxide having an oxygen carrier function to the product of step (c), thereby adjusting the energy band gap of the titanium oxide;
  - (e) dispersing sufficient product from step (d) on a metal to produce a coating on said metal having a thickness of about 15–30 micrometers after drying; and
  - (f) heating the coating for about 6–12 hours at a temperature of about 400–600° C., thereby producing the ferroelectric semiconductive coating;
- applying 440 V and 30 K–100 K Hz alternating current to said plurality of ferroelectric semiconductor plates;
- contacting said gas stream with said ferroelectric semiconductor plates, thereby removing said environmental air pollutants from said gas stream.

8. The method of claim 7, further comprising contacting said gas stream with a spray comprising calcined lime and water before contacting said gas stream with said ferroelectric semiconductor plates.

* * * * *